United States Patent [19]
Chen

[11] Patent Number: 6,068,636
[45] Date of Patent: May 30, 2000

[54] INTRA-INTESTINAL BYPASS GUN

[76] Inventor: Te-Chuan Chen, No. 4-1, Lane 131, Sec. 1 Hang Chou S. Road, Taipei, Taiwan

[21] Appl. No.: 09/296,593

[22] Filed: Apr. 23, 1999

[51] Int. Cl.[7] .................................................. A61B 17/08
[52] U.S. Cl. ............................................................ 606/153
[58] Field of Search ................................... 606/153, 154, 606/155, 156, 148, 150; 623/1, 12

[56] References Cited

U.S. PATENT DOCUMENTS

| | | | |
|---|---|---|---|
| 4,667,673 | 5/1987 | Li | 128/334 |
| 5,376,098 | 12/1994 | Fontayne et al. | 606/153 |
| 5,425,738 | 6/1995 | Gustafson et al. | 606/153 |
| 5,464,415 | 11/1995 | Chen | 606/153 |

OTHER PUBLICATIONS

K. Messmer Munich, vol. 20, pp. 238–242 "European Surgical Research" (1998).
Te–Chuan Chen, Ming–Jui Yang, Shean–Rong Chen, Chih–Peng Chang, and Chau–Hwa Chi, vol. 40, No. 9 pp. 1063–1067 "Valtrac–Secured Intracolonic Bypass Device" (Sep. 1997).

Te–Chuan Chen, Ming–Jui Yang, and Chih–Peng Chang, vol. 38 No. 11 pp. 1214–1216 "New Anastomotic Gun for Biofragmentable Anastomotic Ring in Low Anterior Resection" (Nov. 1995).

*Primary Examiner*—Michael Buiz
*Assistant Examiner*—Vy Q. Bui
*Attorney, Agent, or Firm*—Bacon & Thomas

[57] ABSTRACT

An intra-intestinal bypass gun, which includes a tube body, a gun head unit, and an operation unit, wherein the gun head unit includes a base, a guide rod, a push rod, and a hollow anastomosis rod; the operation unit includes a rotary member, a movabler shaft, a hollow screw cap, and a quick-release connector. Rotating the rotary member causes the movable shaft, the quick-release connector, the guide rod and the hollow anastomosis rod to be moved axially upwards/downwards in opening/closing the head portion of the anastomosis rod so that a bypass tube can be secured with an anastomosis ring to the inside of the intestinal canal during an intra-intestinal bypass operation.

7 Claims, 12 Drawing Sheets

FIG. 12

INTRA-INTESTINAL BYPASS GUN

BACKGROUND OF THE INVENTION

The present invention relates to a medical instrument for intestinal canal operation, and more specifically to such a medical instrument for use with an anastomosis ring in an intra-intestinal bypass operation.

Biofragmentable Anastomosis Ring (called as BAR or Valtrac) is manufactured by Davis & Geck, American Cyanamid Company Danbury, CT06810. This anastomosis ring is safe in use in intestinal anastomosis. Because it decomposes into fragments within 2–3 weeks, and can quickly be discharged out of the bowels, it is popularly accepted. U.S. Pat. No. 5,464,415, entitled "SUTURELESS INTESTINAL ANASTOMOSIS GUN", teaches the use of a gun-base medical instrument for operating an anastomosis ring in an intestinal anastomosis.

SUMMARY OF THE INVENTION

An intra-intestinal bypass gun according to the present invention comprises a tube body, a gun head unit, and an operation unit. The tube body has a first end and a second end. The gun head unit is coupled to the first end of the tube body, comprising a cylindrical base, a hollow guide rod moved in the cylindrical base, a hollow anastomosis rod having a head portion and a tail portion connected to one end of the guide rod in the cylindrical base, and a push rod fastened to the cylindrical base on the inside and suspended inside the head portion of the hollow anastomosis rod. The operation unit comprises a rotary member coupled to the second end of the tube body, a hollow screw cap coupled between the rotary member and the second endpiece of the tube body, a movable shaft coupled to the rotary member and suspended in the tube body and moved axially up and down in the tube body upon rotary motion of the rotary member, and a quick-release connector connected to one end of the movable shaft remote from the rotary member to secure the gun head unit to the movable shaft. When the rotary member is rotated clockwise/counter clockwise, the gun head unit is moved downwards/upwards with the movable shaft relative to the push rod, thereby causing the head portion of the hollow anastomosis rod to be opened/closed.

When used in an operation to remove a part of the diseased of intestinal canal, an artificial bypass tube of elastic film is fastened with its one end to the neck of the anastomosis ring, and the opposite end of the artificial bypass tube is sleeved onto the gun head unit and the tube body, and then the bypass gun is inserted from the anus or the opening of the intestinal canal to a certain distance, and then the operation unit is operated to secure the anastomosis ring to the intestinal canal, enabling waste matter to be discharged out of the intestinal canal through the artificial bypass tube without contaminating the treated area at the intestinal canal. The anastomosis ring is of the known art, and commercially available. The bypass gun of the present invention is simple, practical and safe in use. It eliminates the requirement of a temporary operation of making an opening at the intestinal canal and a secondary operation of closing the opening at the intestinal canal.

DETAILED DESCRIPTION OF THE PREFERRED EMBODIMENT

Figure 1:
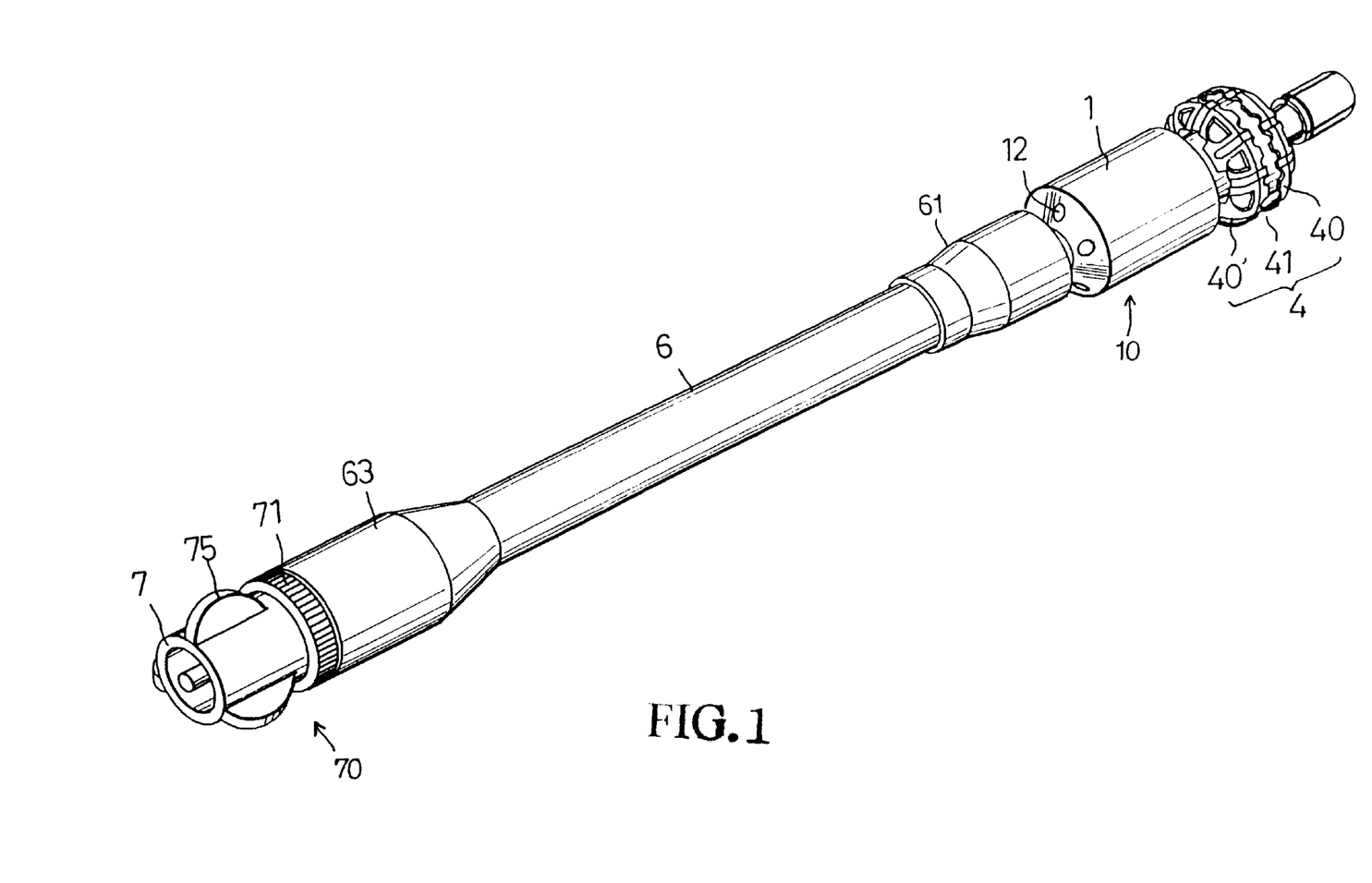
FIG. 1 is a perspective view of the present invention.

Referring to FIG. 1, the present invention is generally comprised of a tube body 6, a gun head unit 10, and an operation unit 70.

Figure 2:
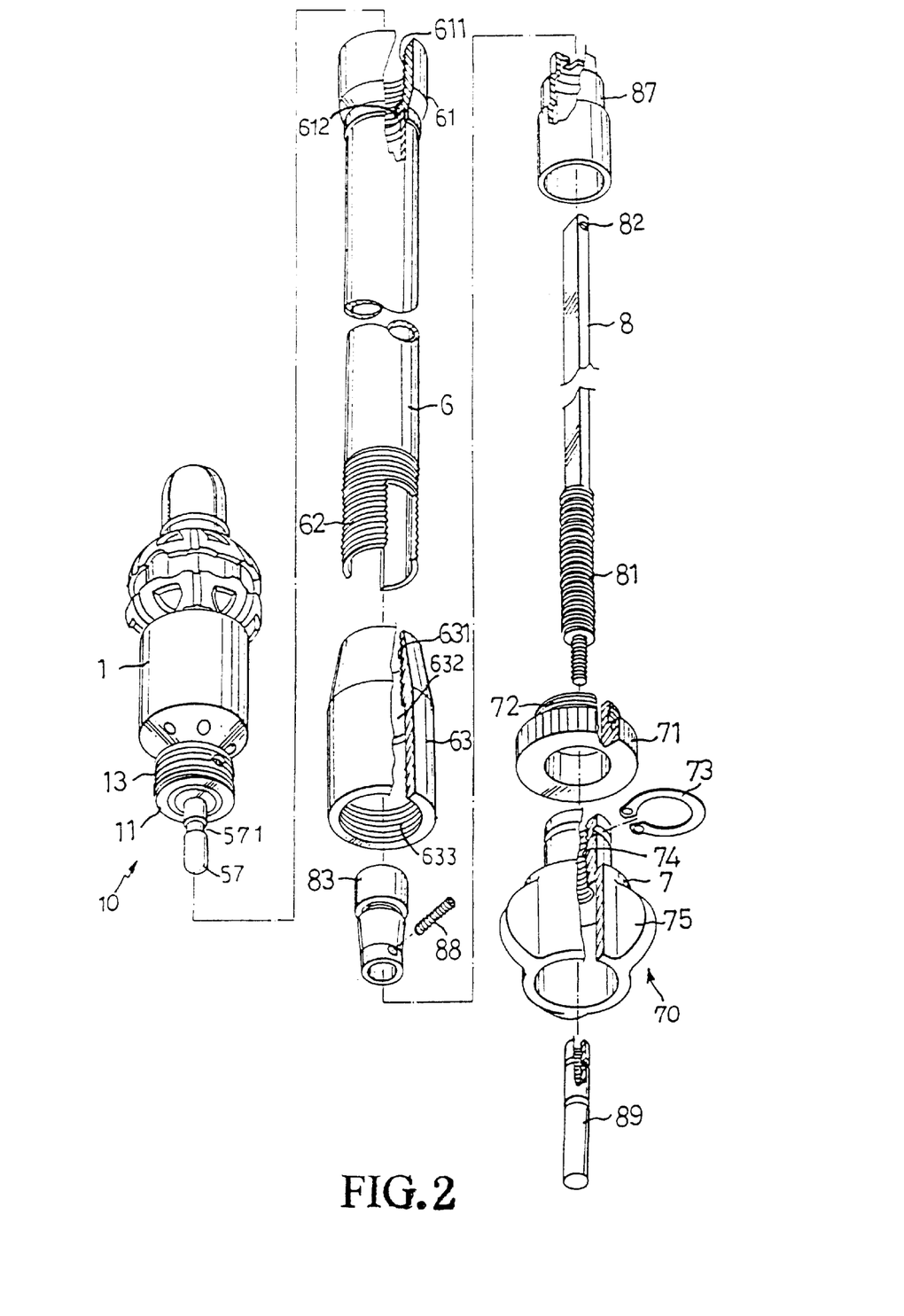
FIG. 2 is an exploded view of the present invention.

Referring to FIG. 2, the tube body 6 has one end terminating in a first endpiece 61, and an opposite end terminating in a second endpiece 63. The first endpiece 61 is a tubular connector having an inner thread 611 and an inside annular flange 612 on its inside wall. The second endpiece 63 is a tubular coupling having an axially extended receiving chamber 632, a first inner thread 631 at one end of the receiving chamber 632, and a second inner thread 633 at an opposite end of the receiving chamber 632. The first inner thread 631 of the second endpiece 63 is threaded onto an outer thread 62 at one end of the body of the tube body 6 remote from the first endpiece 61.

Figure 3:
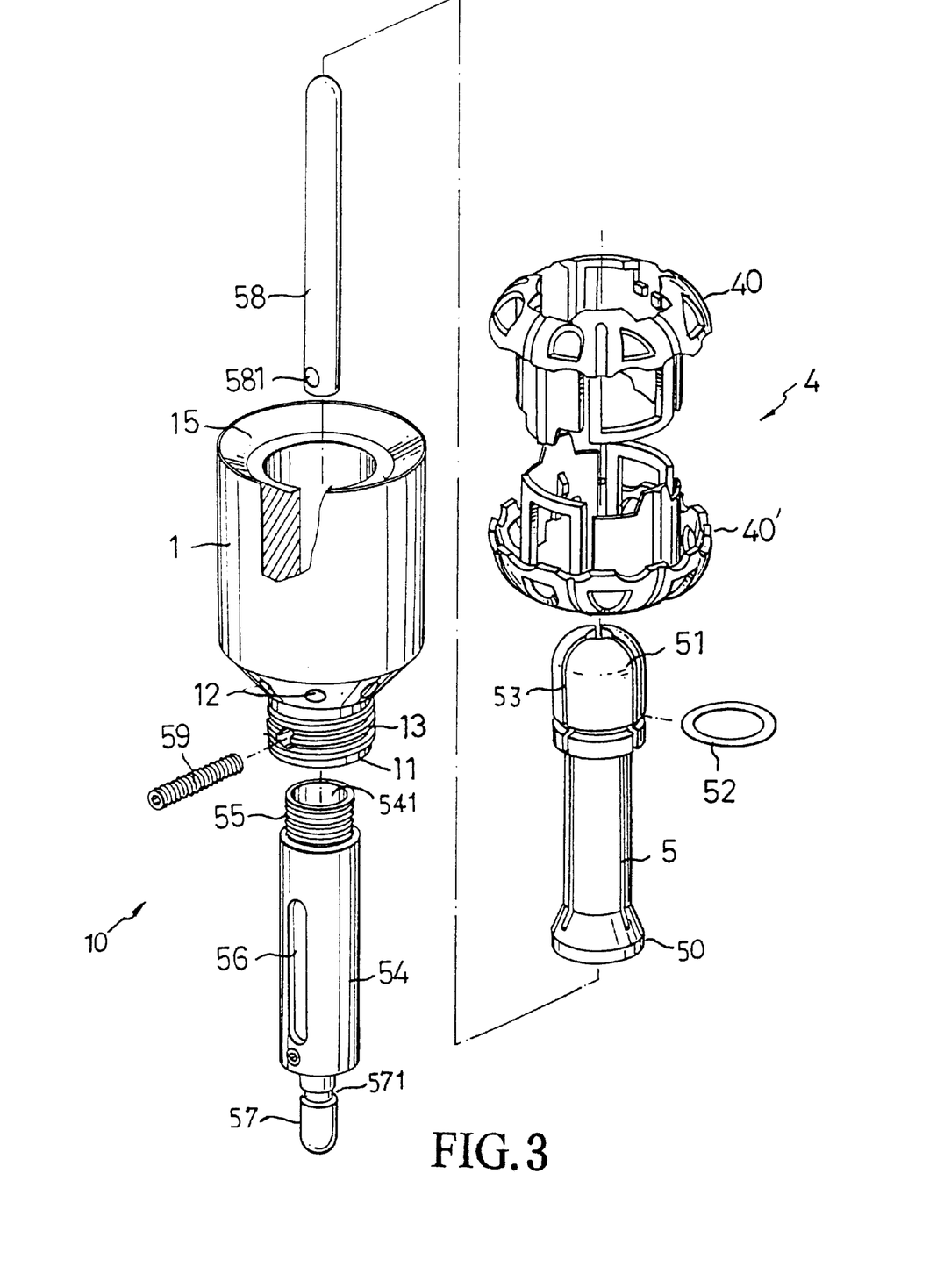
FIG. 3 is an exploded view of the gun head unit according to the present invention.
Figure 4:
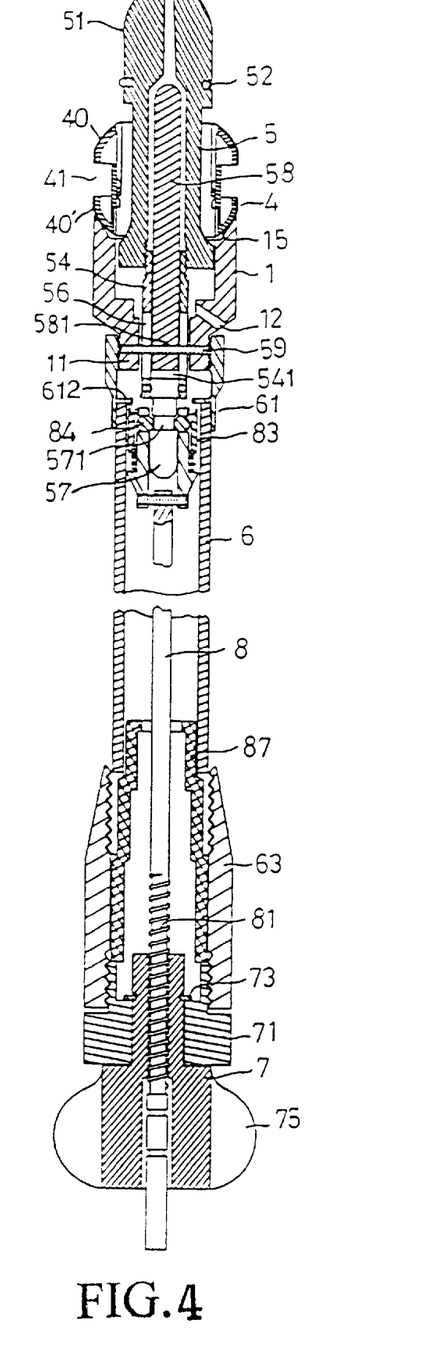
FIG. 4 is a sectional assembly view of the present invention.

Referring to FIGS. 3 and 4 and FIG. 2 again, the gun head unit 10 is coupled to the first endpiece 61 of the tube body 6, comprised of a cylindrical base 1, a guide rod 54, a push rod 58, and a hollow anastomosis rod 5. The anastomosis rod 5 comprises a head portion 51, and a tail portion 50. The tail portion 50 of the anastomosis rod 5 is connected to a threaded coupling portion 55 at one end of the guide rod 54. The push rod 58 has its upper part inserted through the tail portion 50 into the hollow anastomosis rod 5, and its lower part inserted into an axial center hole 541 in the guide rod 54. A fastening element 59 is transversely mounted in a shank 11 at one end of the cylindrical base 1, and inserted through a longitudinal sliding slot 56 at the guide rod 54 and a locating hole 581 at one end of the push rod 58 to secure the push rod 58 and the guide rod 54 to the cylindrical base 1. The cylindrical base 1 comprises a plurality of circular air vents 12 spaced around the periphery adjacent to the shank 11 and disposed in communication with its inside space for exhaust of gas after insertion of the medical instrument into the large intestine. The hollow anastomosis rod 5 is made of flexible material, having a plurality of longitudinal splits 53, that meet at the top center of the head portion 51. An elastic binding ring 52 is mounted on the head portion 51. The elastic binding ring 52 imparts a radial compression force to the head portion 51 of the hollow anastomosis rod 5, thereby causing the longitudinal splits 53 to be closed. The base 1 has a anastomosis ring seat 15, which supports an anastomosis ring 4. The anastomosis ring 4 is comprised of two symmetrical halves 40 and 40', defining a neck 41 on the middle.

Referring to FIGS. 2 and 4 again, the operation unit 70 comprises a rotary member 7, a movable shaft 8, a hollow screw cap 71, and a quick-release connector 83. The hollow screw cap 71 is fastened to the second endpiece 63 of the tube body 6. The quick-release connector 83 is fastened to the gun head unit 10. The rotary member 7 is a hollow, stepped cylinder, having a plurality of wings 75 spaced around its periphery. The guide rod 54 of the gun head unit 10 comprises an endpiece 57 axially extended from its one end remote from the threaded coupling portion 55. The endpiece 57 has an annular groove 571 around its periphery.

Referring to FIG. 2 again, the movable shaft 8 has one end terminating in a screw rod 81, which is threaded into an a screw hole 74 at the rotary member 7. An axial guide 87 is sleeved onto the movable shaft 8 to guide axial movement of the movable shaft 8, and to stop the movable shaft 8 from rotary motion. The axial guide 87 is received in the receiving chamber 632 inside the second endpiece 63 of the tube body 6. An index rod 89 is fastened to the screw rod 81 at one end to indicate the distance of axial movement of the movable shaft 8. The rotary member 7 is secured to screw cap 71 by a clamp 73. The screw cap 71 has a threaded shank 72 threaded into the second inner thread 633 at the second endpiece 63 of the tube body 6. When assembled, the movable shaft 8 can be moved axially by rotating the rotary member 7. Through the wings 75, the rotary member 7 can conveniently be rotated with the hand. The quick-release connector 83 is sleeved onto the top end (the end remote from the screw rod 81) of the movable shaft 8, and secured to a screw hole 82 near the top end of the movable shaft 8 by a screw 88.

Referring to FIG. 4 again, the shank 11 of the cylindrical base 1 has an outer thread 13 threaded into the inner thread 611 at the first endpiece 61 of the tube body 6. The quick-release connector 83 of the operation unit 70 can releasably be connected to the endpiece 57 of the guide rod 54 of the gun head unit 10, i.e., the gun head unit 10 can be quickly and releasably connected to the operation unit 70. The quick-release connector 83 comprises a plurality of steel balls 84 on the inside. After insertion of the endpiece 57 of the guide rod 54 of the gun head unit 10 into the quick-release connector 83, the steel balls 84 are forced to engage into the annular groove 571 at the endpiece 57 of the guide rod 54, thereby causing the gun head unit 10 to be secured to the operation unit 70.

Figure 5:
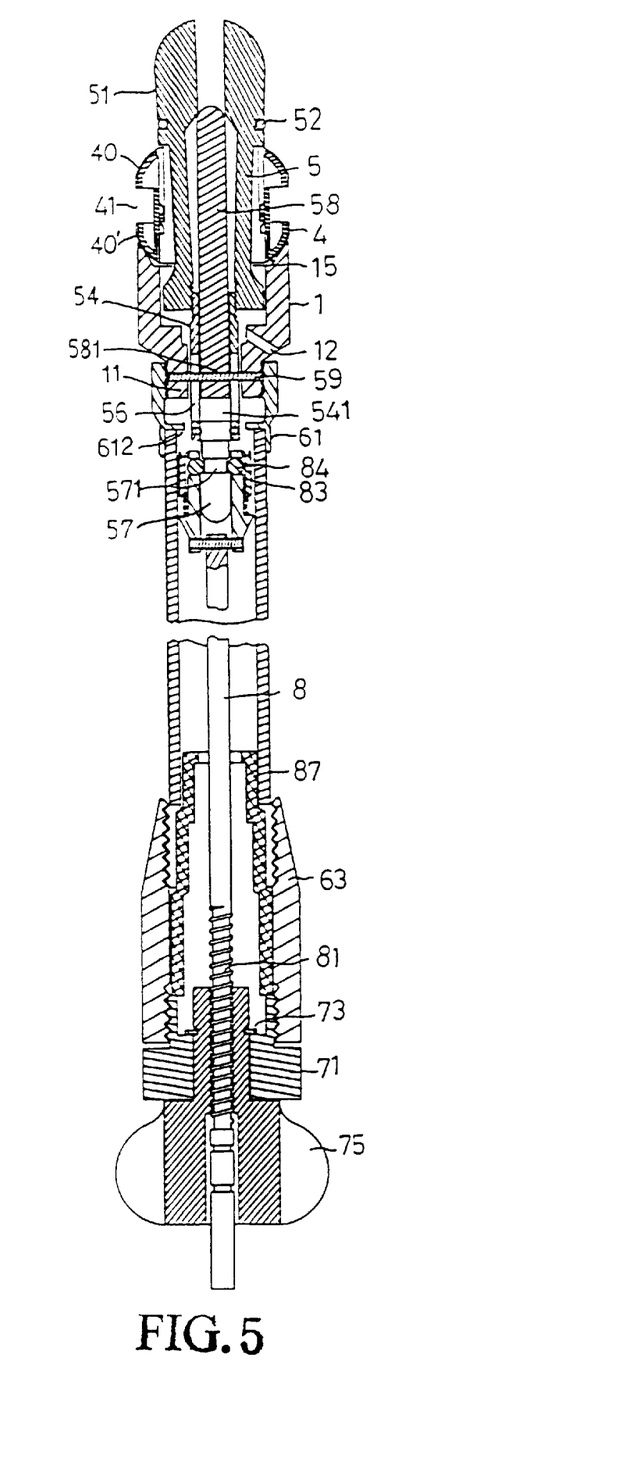
FIG. 5 is similar to FIG. 4 but showing the anastomosis rod lowered, the head portion of the anastomosis rod opened.

Referring to FIG. 5 and FIG. 4 again, rotating the rotary member 7 forwards/backwards causes the movable shaft 8, the screw rod 81, the guide rod 54 and the anastomosis rod 5 to be moved axially upwards/downwards. When the-anastomosis rod 5 is lowered to the position shown in FIG. 5, the split head portion 51 of the anastomosis rod 5 is stretched open by the push rod 58 to secure the anastomosis ring 4 in place. On the contrary, when the anastomosis rod 5 is lifted to the position shown in FIG. 4, the push rod 58 is released from the split head portion 51 of the anastomosis rod 5, and returned to the closed position by the compression force of the elastic binding ring 52, and therefore the anastomosis ring 4 is released from the constraint of the split head portion 51 of the anastomosis rod 5.

Figure 6:
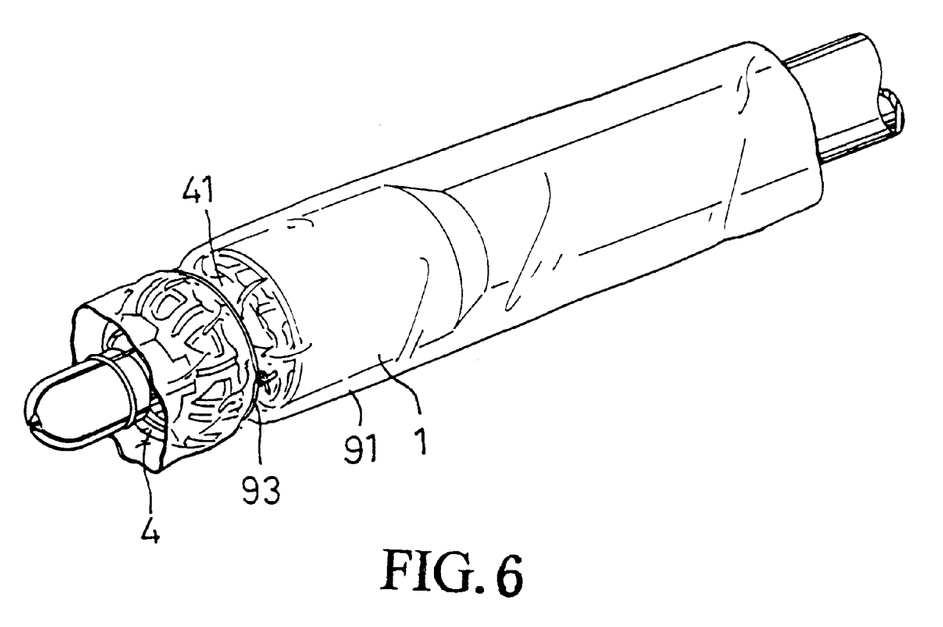
FIG. 6 illustrates an artificial bypass tube fastened to the anastomosis ring and sleeved onto the tube body according to the present invention.

Referring to FIG. 6, when in use, an artificial bypass tube 91 is sleeved onto the gun head unit 10, and then secured to the neck 41 of the anastomosis ring 4 by a suture thread 93.

Figure 7:
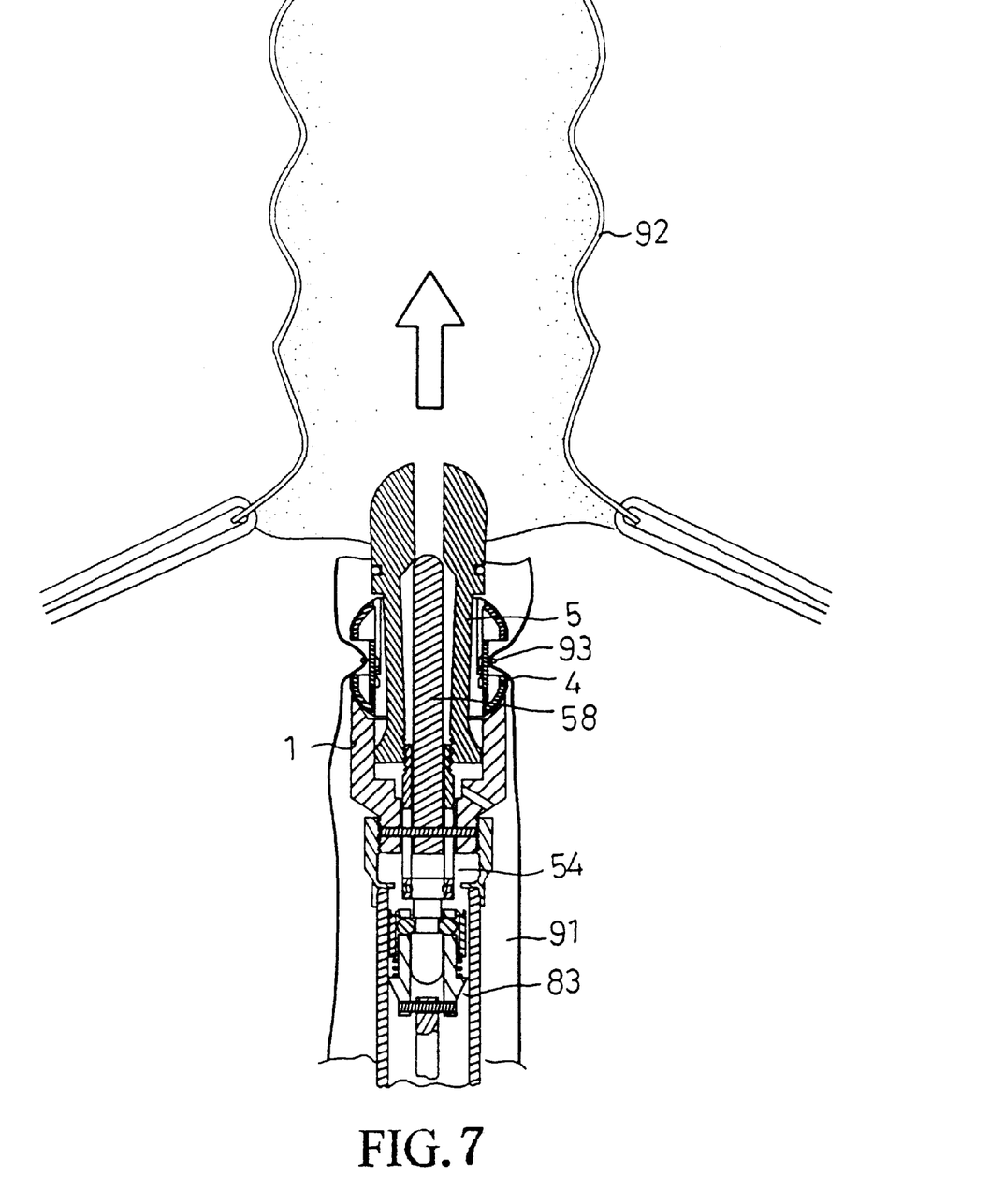
FIG. 7 is an applied view of the present invention, showing the intestinal canal opened, the bypass gun inserted into the intestinal canal.
Figure 8:
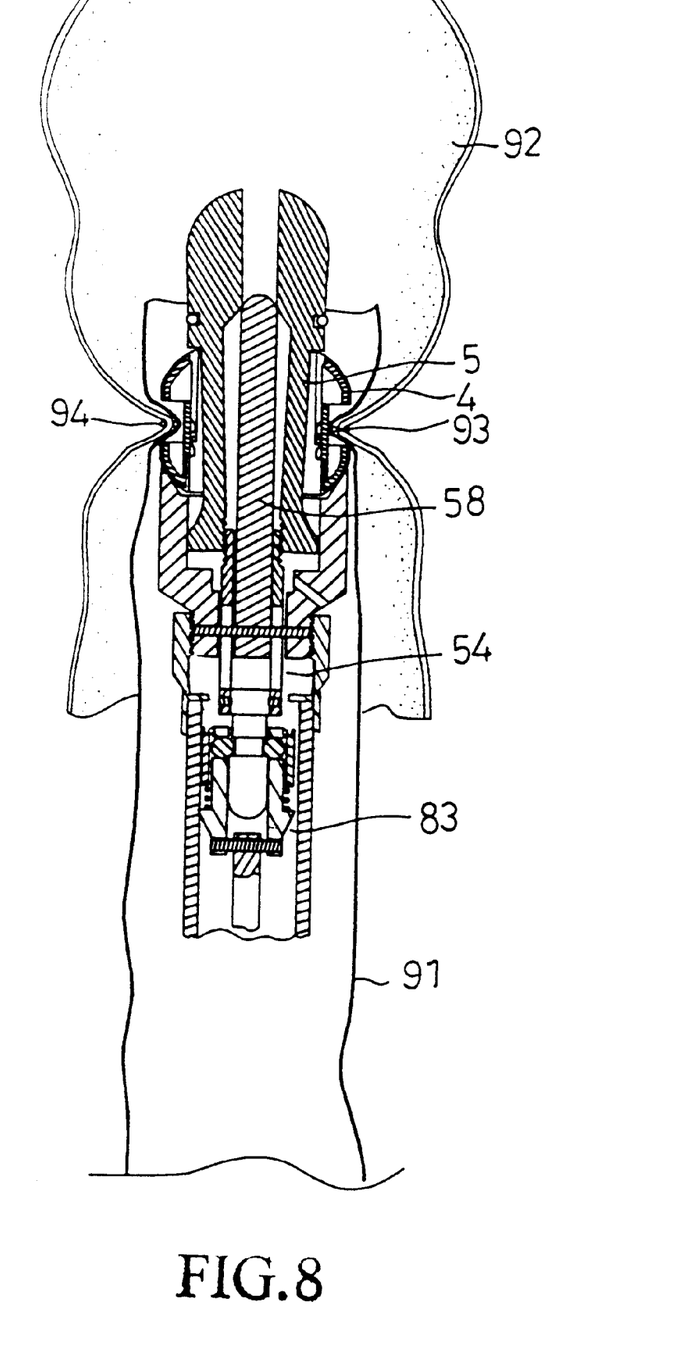
FIG. 8 is another applied view of the present invention, showing the connection of the anastomosis ring, the artificial bypass tube and the intestinal canal.

Referring to FIGS. 7 and 8, the artificial bypass tube 91 is inserted with the anastomosis ring 4 into the intestinal canal 92 at a certain distance, then a suture thread 94 is wound round the outside wall of the intestinal canal 92 and tied up at the neck 41 of the anastomosis ring 4.

Figure 9:
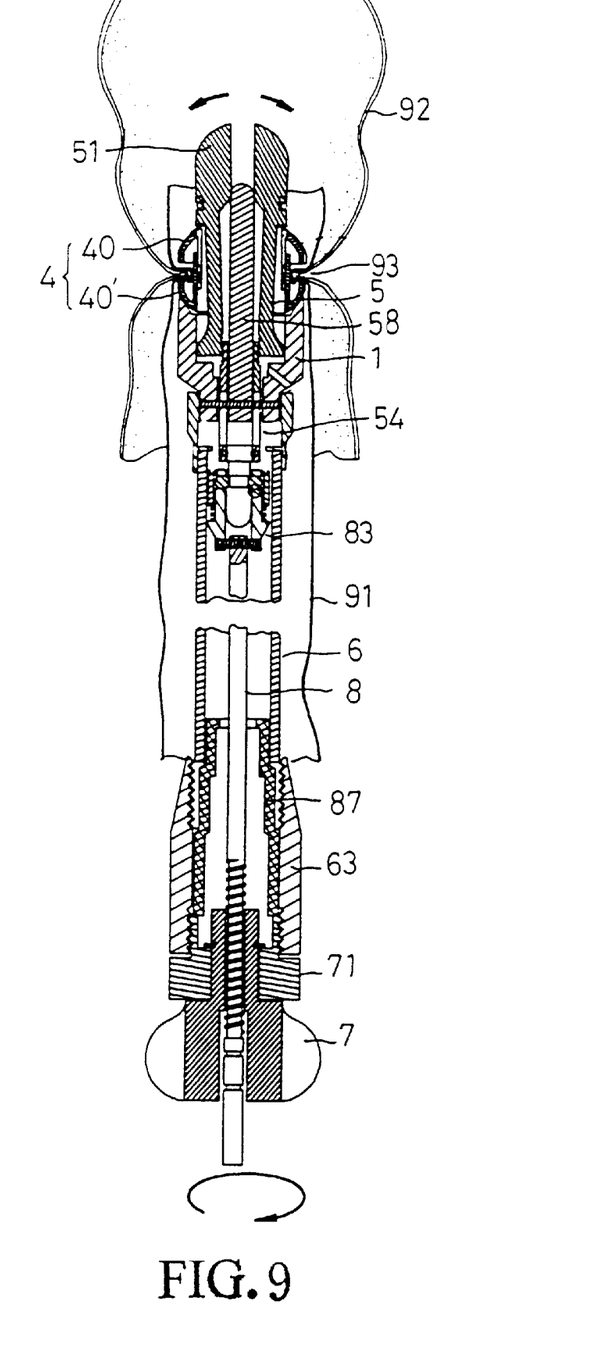
FIG. 9 illustrates the rotary member rotated in clockwise direction, the anastomosis ring fastened up according to the present invention.

Referring to FIG. 9, the rotary member 7 is rotated to lower the movable shaft 8, the guide rod 54 and the anastomosis rod 5, enabling the split head portion 51 of the anastomosis rod 5 to be stretched open by the push rod 58, and the two symmetrical halves 40 and 40' of the anastomosis ring 4 to be forced against each other, and therefore the intestinal canal 92, the artificial bypass tube 91 and the anastomosis ring 4 are firmly retained together.

Figure 10:
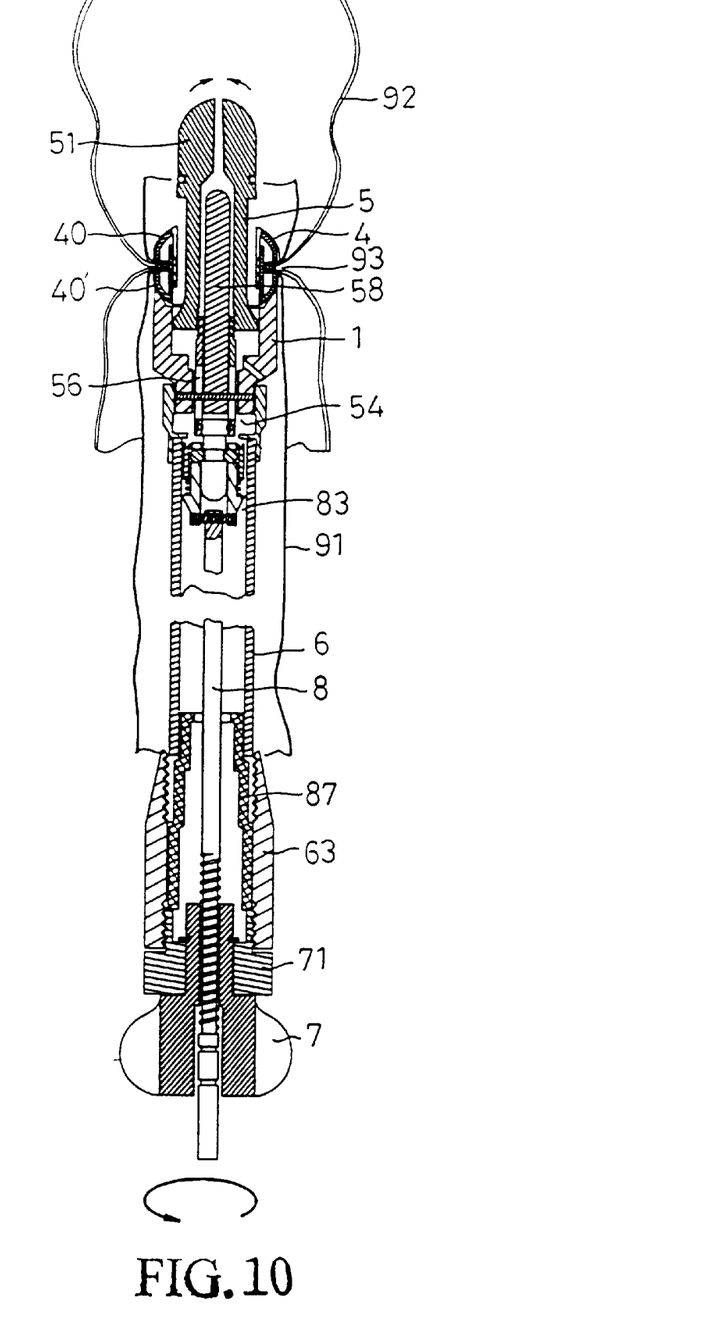
FIG. 10 shows the rotary member rotated in counter clockwise direction, head portion of the anastomosis rod returned to its former shape.
Figure 11:
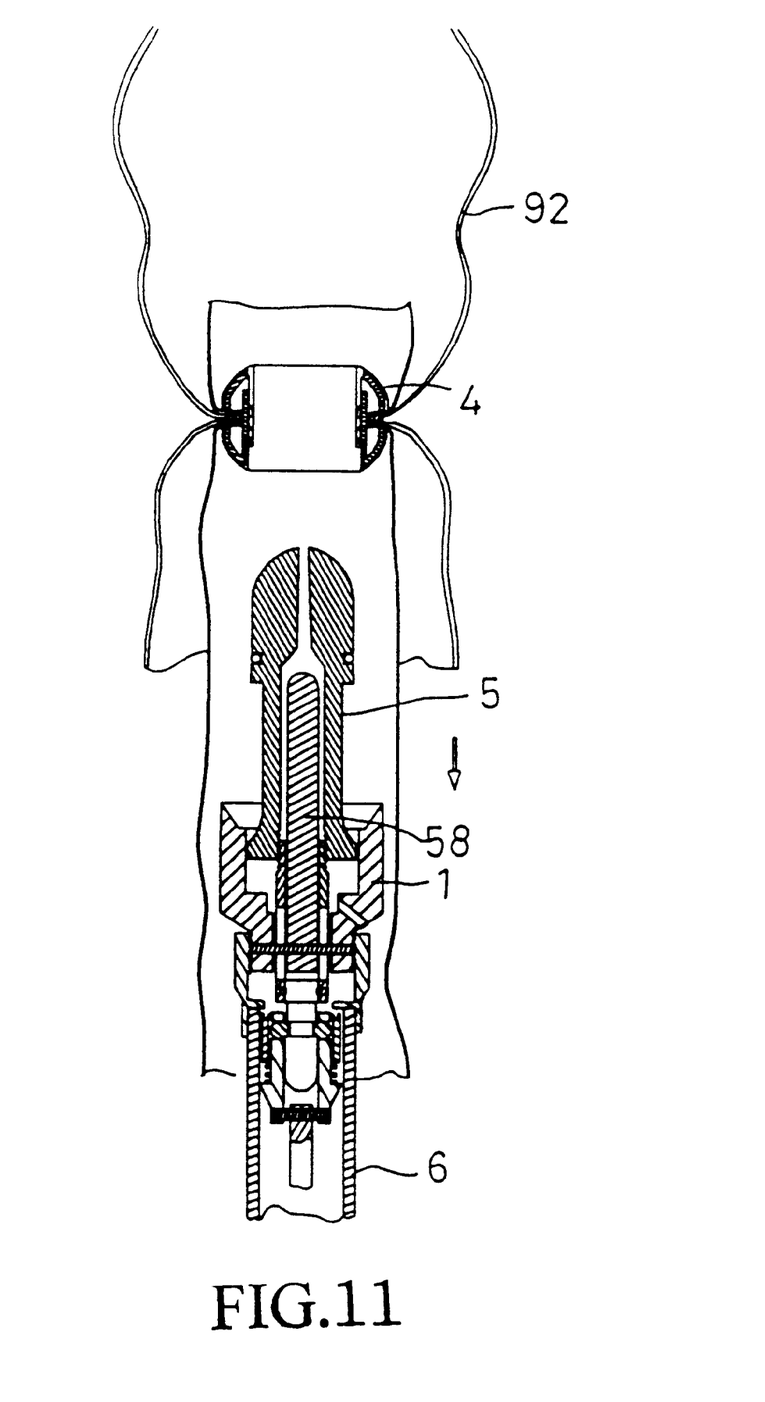
FIG. 11 shows the operation finished, the bypass gun disconnected from the intestinal canal.
Figure 12:
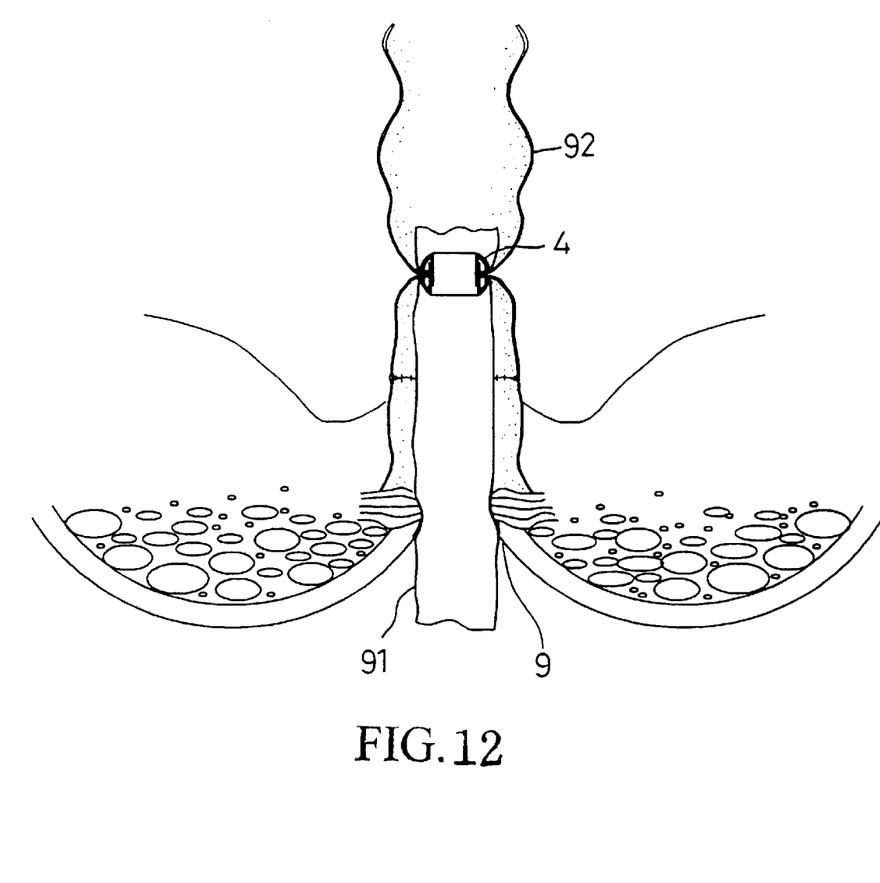
FIG. 12 is a schematic drawing showing the intra-intestinal bypass gun operation finished.

Referring to Figures from 10 through 12, the rotary member 7 is then rotated in the reversed direction to lift the movable shaft 8, the guide rod 54 and the anastomosis rod 5, so as to release the split head portion 51 of the anastomosis rod 5 from the push rod 58, enabling the medical instrument to be removed from the intestinal canal 92 and artificial bypass tube 91.

While only one embodiment of the present invention has been shown and described, it will be understood that various modifications and changes could be made thereunto without departing from the spirit and scope of the invention disclosed.

What is claimed is:

1. An intra-intestinal bypass gun comprising:

a tube body having a first end and a second end;

a gun head unit coupled to the first end of said tube body, said bun head unit comprising a cylindrical base, a hollow guide rod moved in said cylindrical base, a hollow anastomosis rod having a head portion and a tail portion connected to one end of said guide rod, and a push rod fastened to said cylindrical base on the inside and suspended inside the head portion of said hollow anastomosis rod; and an operation unit, said operation unit comprising a rotary member coupled to the second end of said tube body, a hollow screw cap coupled between said rotary member and the second end of said tube body, a movable shaft coupled to said rotary member and suspended in said tube body and moved axially up and down in said tube body upon rotary motion of said rotary member, and a quick-release connector connected to one end of said movable shaft remote from said rotary member to secure said gun head unit to said movable shaft;

wherein when said rotary member is rotated in one direction, said gun head unit is moved downwards with said movable shaft relative to said push rod, thereby causing the head portion of said hollow anastomosis rod to be stretched open by said push rod; when said rotary member is rotated in the reversed direction, said gun head unit is moved upwards with said movable shaft, thereby causing the head portion of said hollow anastomosis rod to be released from said push rod, wherein said guide rod comprises an annular groove around the periphery of an endpiece at one end thereof for coupling to said quick-release connector, and said quick-release connector has a plurality of steel balls for engaging into the annular groove at the endpiece of said guide rod to secure said guide rod to said operation unit, and wherein the base of said gun head unit comprises an anastomosis ring seat, which supports an anastomosis ring.

2. The intra-intestinal bypass gun of claim 1 wherein said hollow anastomosis rod is made of elastic material, comprising a plurality of longitudinal splits met at the top center of said head portion, and an elastic binding ring mounted on said head portion.

3. The intra-intestinal bypass gun of claim 1 wherein said movable shaft has one end terminating in a screw rod threaded into a screw hole at one end of said rotary member.

4. The intra-intestinal bypass gun of claim 1 wherein said operation unit further comprises an axial guide mounted inside said tube body to guide axial movement of said movable shaft.

5. The intra-intestinal bypass gun of claim 4 wherein the second end of said tube body comprises a receiving chamber, which receives said axial guide.

6. The intra-intestinal bypass gun of claim 1 wherein said operation unit further comprises an index rod connected to said movable shaft at one end for indicating the distance of movement of said movable shaft.

7. The intra-intestinal bypass gun of claim 1 wherein said anastomosis ring is comprised of two symmetrical halves coupled together and moved relative to each other and defining a neck therebetween.

* * * * *